United States Patent [19]

Cartwright

[11] 4,276,767
[45] Jul. 7, 1981

[54] EROSION POTENTIAL DETERMINATIONS

[76] Inventor: Frederick D. Cartwright, 506 Lake Club Apts., Lake Rd., Germiston, Transvaal, South Africa

[21] Appl. No.: 60,858

[22] Filed: Jul. 26, 1979

[30] Foreign Application Priority Data

Aug. 4, 1978 [ZA] South Africa ................. 78/4565
Apr. 23, 1979 [ZA] South Africa ................. 79/1906

[51] Int. Cl.³ ............................................. G01N 3/56
[52] U.S. Cl. ............................................. 73/7
[58] Field of Search .......................... 73/7, 86, 61.2

[56] References Cited

U.S. PATENT DOCUMENTS

| | | | |
|---|---|---|---|
| 2,712,751 | 7/1955 | Bracco et al. | 73/61.2 X |
| 2,907,200 | 10/1959 | Roberts et al. | 73/7 |
| 3,229,498 | 1/1966 | Oakes | 73/7 |

OTHER PUBLICATIONS

Houston, J. T. *A Sandblast Abrasion Test...*, In materials Research & Standards, pp. 17-20 & 42, Aug. 1970, vol. 10 (8).

*Primary Examiner*—Gerald Goldberg
*Assistant Examiner*—Joseph W. Roskos
*Attorney, Agent, or Firm*—Stevens, Davis, Miller & Mosher

[57] ABSTRACT

This invention relates to a method and apparatus for determining the erosion potential of particulate material such as that contained in a mine dump or erosive farmland. The method consists in directing a jet of fluid such as water or air onto the surface of the material from a fixed distance at a fixed pressure or range of pressures and measuring the parameters of the jet against a scale when the jet produces a predetermined effect on the material under test. The apparatus includes a portable accumulator for holding the fluid under pressure, a nozzle through which the fluid may be discharged from the accumulator, means between the accumulator and nozzle for adjusting fluid flow between the two and a portable and adjustable frame such as a tripod on which the apparatus is mounted.

8 Claims, 1 Drawing Figure

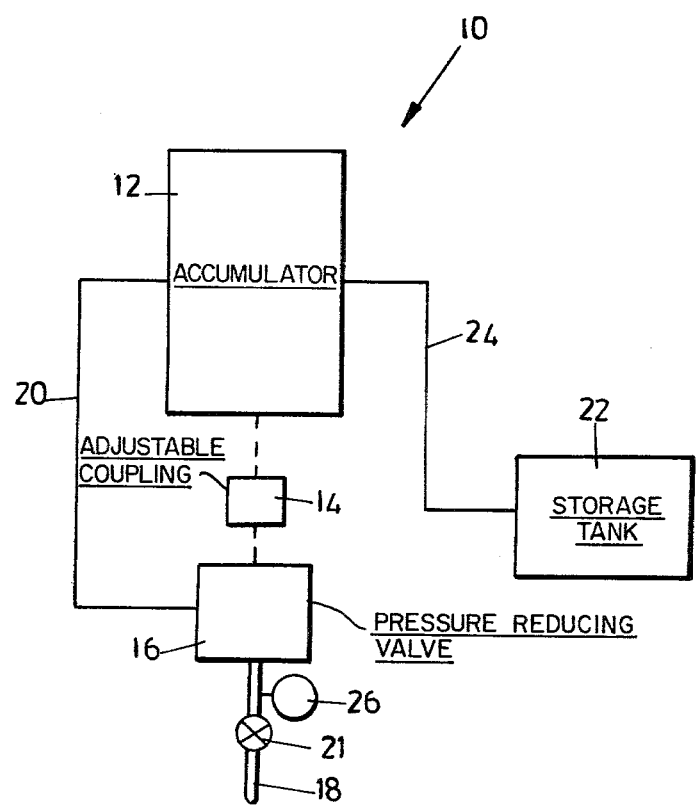

EROSION POTENTIAL DETERMINATIONS

FIELD OF THE INVENTION

This invention relates to a method of determining the erosion potential of particulate material contained in mining residue deposits, farm lands, civil engineering works and the like and to apparatus for carrying out the method.

BACKGROUND TO THE INVENTION

Rainfall simulators for determining the erosion potential of farm lands are known and consist fundamentally of a frame including a plurality of elevatd and downwardly directed spray nozzles for simulating rainfall and means for moving the frame backwards and forwards on a track over the soil area being tested. The simulators additionally include troughs in which the run off from the test area is collected and measured against the energy of the water sprays. The rainfall simulators are cumbersome, expensive and need to be operated for a considerable period of time before a reasonably accurate measurement of the erosion potential of the test area may be determined. Additionally, the simulators described above are unsuitable for use on relatively steep slopes such as the sides of mine dumps and on uneven terrain. In situations such as this the erosion potential is inaccurately measured over a long period by means of strategically placed collecting troughs which are filled by material which has become dislodged by natural rain erosion.

Both of the above methods of measuring erosion potential give no indication of the possible effect of wind erosion on the material in the area being tested.

OBJECT OF THE INVENTION

It is the object of this invention to provide a method of and apparatus for determining the erosion potential of particulate material in a test area which will minimise the disadvantages mentioned above.

SUMMARY OF THE INVENTION

A method of determining the erosion potential of a particulate material according to the invention includes the steps of directing a jet of fluid from a nozzle onto the surface of the material and measuring the parameters of the jet against a scale when the jet produces a predetermined effect on the material being tested.

In a preferred form of the invention the method includes the steps of locating the nozzle a fixed distance from the surface of the material and progressively increasing the pressure of the jet until the particles of the material at the surface of the material begin to disperse and measuring the pressure of the fluid at the point of dispersion of the particles against a scale of known erosion pressures to determine the erosion potential of the material. Preferably, the fluid jet is directed vertically onto the surface of the material being tested.

To minimise the effects of moisture on the material being tested and to obtain consistent results it is preferable to heat dry the surface of the material in the test area prior to the commencement of the test.

Preferably, the fluid used in carrying out the test is a liquid such as water.

According to the invention apparatus for determining the erosion potential of particulate material includes a fluid nozzle, means for controlling fluid flow from the nozzle, means for supplying fluid under pressure to the nozzle and a frame for holding the nozzle in a fixed relationship relatively to the surface of the material to be tested. The fluid supply means may consist of an accumulator for containing fluid such as water under pressure and conveniently the apparatus includes a portable self-contained pump for charging the accumulator with fluid under pressure.

In one form of the invention the nozzle is held to the frame by means which is adapted to permit adjustment of the nozzle towards and away from the surface of the material and angular adjustment relatively to the axis on which the nozzle is movable towards and away from the surface.

Further according to the invention the apparatus includes means for varying the pressure of fluid leaving the nozzle in use and an indicator for indicating the pressure of fluid leaving the nozzle.

In this specification and in the claims the term fluid is to be taken to mean either a liquid or a gas and does not include flowable particulate material such as sand, shot and the like.

BRIEF DESCRIPTION OF THE DRAWING

An embodiment of the invention is now described by way of example with reference to the drawing which is a diagrammatic representation of the apparatus of the invention.

DETAILED DESCRIPTION OF THE INVENTION

The apparatus of the invention is shown in the drawing to consist of a mechanically interconnected arrangement indicated generally at 10 which includes an accumulator 12 for storing a quantity of water under pressure, an adjustable coupling 14, a pressure reducing valve 16 and a water jet nozzle 18 which is fixed and connected to the outlet of the valve 16. A hydraulic line 20 connects the outlet of the accumulator 12 to the valve 16. The nozzle 18 carries a stop cock 21.

The coupling 14 is adapted to permit movement of the valve 16 and nozzle 18 towards and away from the accumulator and also to permit angular adjustments of the nozzle relatively to the axis on which the valve and nozzle are movable towards and away from the accumulator.

The arrangement 10 is mounted on an adjustable tripod, which is not shown in the drawing, with the nozzle 18 downwardly directed towards the surface on which the tripod rests in use.

A portable water storage tank 22 which includes a hand operated pump and pressure gauge forms part of the apparatus and is connected to the inlet of the accumulator 12 by means of a removable flexible hydraulic line 24.

In use, the tank 22 is filled with water and the apparatus transported to the test site. At the site the tripod carrying the arrangement 16 is erected with the nozzle directed vertically onto the surface of the material on which the tripod is standing. The nozzle is then adjusted by means of the coupling 14 and a spacer to be situated with its outlet at a predetermined distance from the surface.

The tank 22 is then connected to the accumulator 12 by means of the line 24 and the accumulator charged with water from the tank 22. The tank 22 may then be disconnected from the apparatus to facilitate its portability.

The valve 16 includes means, not shown in the drawing, for controlling the flow of water from the valve 16. A pressure gauge 26 for indicating the pressure of water leaving the nozzle is connected into a line between the valve 16 and the stop cock 21.

With the apparatus located in position at the test site and the accumulator fully charged and the cock 21 open, the controller on the valve 16 is opened to allow a jet of water to impinge on the material under test. To avoid a burst effect on the material under test the controller is opened slowly and at a predetermined rate. As soon as particles of the material under test begin to disperse in the impact zone of the water jet the pressure on the indicator 26 is recorded. This reading taken against known parameters such as the distance of the nozzle outlet from the surface of the material, nozzle area and the rate of water discharge from the nozzle, is measured against a table of standard erosion potentials to arrive at the erosion potential of the material under test.

Obviously, the moisture content at the surface of the material being tested will widely influence the results of the tests and to minimise this potential error source the test area is flame dried by means of a low pressure burner.

To ensure vertical nozzle direction the apparatus could include a liquid level which is suitably fixed to the valve 16.

Other tests which have not been mentioned in this specification such as directing the water jet from the nozzle normally or at an angle other than vertically onto the surface of the material may be useful in specific circumstances and have not been described as the tests will generally be specific to a particular situation and the parameters of the test will vary from situation to situation.

Not only do the tests described above provide an indication, within acceptable limits, of the rain water erosion potential of the material under test but also an indication of the consolidation of the surface particles of the material and so the wind erosion potential of the material.

The invention provides means for the quick and simple performance of a number of erosion tests at a specific site in order to determine a mean or range of erosion potentials for that site and also to locate zones of the material which may require special treatment as a result of a greater or lesser tendency of the material to erode in these zones.

Although the above description of both the apparatus and tests which may be carried out with the apparatus refers only to the use of water as a test material, compressed air will serve equally well and may, in fact, be preferable to water as a test material in certain circumstances.

I claim:

1. A method of determining the erosion potential of particulate material including the steps of directing a jet of fluid onto the surface of the material from a nozzle located a fixed distance from the surface of the material, progressively increasing the pressure of the jet from zero pressure until particles of material at the surface begin to disperse and measuring the pressure of the fluid leaving the jet when the particles of the material begin to disperse against a scale of known erosion pressures to determine the erosion potential of the material.

2. A method as claimed in claim 1 including the step of directing the fluid jet vertically onto the surface of the material being tested.

3. A method as claimed in claim 1 including the step of heat drying the surface of the material to be tested prior to the commencement of the test.

4. A method as claimed in claim 1 in which the fluid is a liquid.

5. Portable apparatus for determining the erosion potential of a particulate material including a fluid nozzle, a frame on which the nozzle is mounted and directed towards the surface on which the frame rests in use, means on the frame for varying the distance of the nozzle from the surface on which the frame rests, a portable reservoir for fluid, manually operable means for pressurizing fluid in the reservoir, a fluid line connecting the reservoir to the nozzle, a valve in the line for varying the pressure of fluid from the reservoir to the nozzle, said valve being operable to progressively increase the pressure of the fluid leaving said nozzle from zero pressure, and a fluid pressure indicator in the line downstream of the valve.

6. Apparatus as claimed in claim 5 in which the reservoir is an accumulator.

7. Apparatus as claimed in claim 5 in which the nozzle is attached to the frame by means adapted to permit angular adjustment of the nozzle direction.

8. Apparatus as claimed in claim 5 in which the frame is an adjustable tripod.

* * * * *